US012721693B2

(12) United States Patent
Dardenne et al.

(10) Patent No.: US 12,721,693 B2
(45) Date of Patent: Sep. 1, 2026

(54) METHOD AND SYSTEM FOR PROVIDING ANATOMICAL LANDMARKS OF A SUBJECT'S BODY PART

(71) Applicants: CENTRE HOSPITALIER REGIONAL ET UNIVERSITAIRE DE BREST, Brest (FR); UNIVERSITÉ DE BRETAGNE OCCIDENTALE, Brest (FR); INSERM (INSTITUT NATIONAL DE LA SANTÉ ET DE LA RECHERCHE MÉDICALE), Paris (FR)

(72) Inventors: Guillaume Dardenne, Guipavas (FR); Hoel Letissier, Brest (FR); Jérôme Ogor, Brest (FR); Eric Stindel, Plougonvelin (FR)

(73) Assignees: CENTRE HOSPITALIER RÉGIONAL ET UNIVERSITAIRE DE BREST, Brest (FR); UNIVERSITÉ DE BRETAGNE OCCIDENTALE, Brest (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 321 days.

(21) Appl. No.: 18/253,316

(22) PCT Filed: Nov. 17, 2021

(86) PCT No.: PCT/EP2021/081939

§ 371 (c)(1),
(2) Date: May 17, 2023

(87) PCT Pub. No.: WO2022/106446

PCT Pub. Date: May 27, 2022

(65) Prior Publication Data

US 2024/0008951 A1 Jan. 11, 2024

(30) Foreign Application Priority Data

Nov. 18, 2020 (EP) .................................... 20306404

(51) Int. Cl.
*A61B 90/00* (2016.01)
*A61B 34/10* (2016.01)

(52) U.S. Cl.
CPC ............. *A61B 90/39* (2016.02); *A61B 34/10* (2016.02); *A61B 2034/105* (2016.02); *A61B 2090/3937* (2016.02)

(58) Field of Classification Search
CPC ...... A61B 2034/2065; A61B 2090/364; A61B 8/5246; A61B 2090/363;
(Continued)

(56) References Cited

U.S. PATENT DOCUMENTS

2015/0051489 A1* 2/2015 Caluser .................... A61B 8/13 600/440
2016/0278868 A1 9/2016 Berend et al.
(Continued)

FOREIGN PATENT DOCUMENTS

WO 2020163318 A1 8/2020

OTHER PUBLICATIONS

Cook AC, Anderson RH. Attitudinally correct nomenclature. Heart. Jun. 2002;87(6):503-6. doi: 10.1136/heart.87.6.503. PMID: 12010926; PMCID: PMC1767134 (Year: 2002).*
(Continued)

*Primary Examiner* — John D Li
(74) *Attorney, Agent, or Firm* — Maier & Maier, PLLC

(57) ABSTRACT

A computer-implemented method and a system for providing anatomical landmarks of a subject's body part using a set
(Continued)

of measures previously acquired by an ultrasound device including at least one fiducial marker and an imaging sensor. Also, a non-transitory computer readable medium including instructions which, when the program is executed by a computer, cause the computer to carry out the method.

15 Claims, 3 Drawing Sheets

(58) Field of Classification Search
CPC ...... A61B 2090/3937; A61B 2034/105; A61B 90/39; A61B 34/10
See application file for complete search history.

(56) References Cited

U.S. PATENT DOCUMENTS

2019/0133791 A1* 5/2019 Yadav .................... A61B 34/32
2019/0307518 A1 10/2019 Schotzko et al.
2020/0320721 A1* 10/2020 Holladay ............... A61B 90/39
2020/0320751 A1* 10/2020 Siemionow ............... G06T 7/11
2022/0117663 A1* 4/2022 Mcguan ............... G09B 19/003
2022/0351824 A1* 11/2022 Weissberger .......... G16H 10/60

OTHER PUBLICATIONS

International Search Report and Written Opinion issued on Dec. 22, 2021, in corresponding International Patent Application No. PCT/EP2021/081939, 9 pages.

* cited by examiner

METHOD AND SYSTEM FOR PROVIDING ANATOMICAL LANDMARKS OF A SUBJECT'S BODY PART

FIELD

The present invention pertains to the field of image analysis. In particular, the invention relates to pre-operative image analysis for providing anatomical landmarks of a subject's body part to be used for the planning of an orthopedic surgery.

BACKGROUND

Replacement arthroplasty or joint replacement surgery, is a procedure of orthopedic surgery in which an arthritic or dysfunctional joint surface is replaced with an orthopedic prosthesis. For example, total shoulder arthroplasty aims to replace the pathological joint with a prosthesis composed of a glenoidal part and a humeral part.

These prostheses are nowadays positioned and dimensioned according to the same criteria whatever the patients are. However, especially in the case of the shoulder, different daily positions have a significant impact on the post-operative stability of the implant. The scapula may, for example, have a different position depending on the functional balance of the patient, and these differences may have consequences on the relative functional orientation between the humeral and glenoidal implants, and thus on the possible post-operative range of motion. Consequently, positioning the prostheses in the same way for all patients seems to be not appropriate.

Taking functional parameters into account during planning is therefore essential in order to identify the best prosthetic positioning for a given patient in order to optimize the post-operative prosthetic range of motion.

Today, there is no simple, reliable, precise and non-invasive solution for estimating the prosthetic range of motion of a joint in daily functional positions, for instance, standing or sitting.

The present invention proposes a method for estimating these functional parameters without the prior art drawbacks.

SUMMARY

The present invention relates to a computer-implemented method for providing anatomical landmarks of a subject's body part, said method comprising:

- receiving a set of measures previously acquired by an acquisition system comprising: an ultrasound device, at least one fiducial marker and an imaging sensor; said set of measures comprising:
  - at least one first ultrasound image comprising a first landmark and at least one first image acquired by the imaging sensor simultaneously to the first ultrasound image;
  - at least one second ultrasound image comprising a second landmark and at least one second image acquired simultaneously to the second ultrasound image;
  - at least one third ultrasound image comprising a third landmark and at least one third image acquired simultaneously to the third ultrasound image;
  - wherein the first, second and third image comprises the at least one fiducial marker;
  - at least one fourth image comprising at least one portion of the body part of the subject;

- for each ultrasound image:
  - using the fiducial marker in the associated image for calculating the position and spatial orientation of the ultrasound image in a referential of the imaging sensor;
  - identifying the position of the associated landmark in the ultrasound image and using the position and spatial orientation of the ultrasound image for calculating the position of the landmark in the referential of the imaging sensor;
- calculating the spatial orientation of a transversal plane in the referential of the imaging sensor;
- calculating the spatial orientation of a sagittal plane in the referential of the imaging sensor;
- using the position and spatial orientation of the transversal and sagittal plane to calculate the position and spatial orientation of a coronal plane in the referential of the imaging sensor;
- outputting the anatomical landmarks of a subject's body part comprising at least the position of the first, second and third landmark, and the spatial orientation of the transversal, sagittal and coronal plane in the referential of the imaging sensor.

Advantageously the present method allows to obtain essential information on the position and spatial orientation of the anatomical landmarks of a subject's body part and the three anatomical planes in one same referential in a non-invasive, easy to implement and radiation less way thanks to the use of only an imaging sensor and an ultrasound device trackable thanks to the fiducial marker. Indeed, other methods using for example other standard imaging technics such as CT-scan, X-ray radiography or MRI are all expensive, require cumbersome machines and dedicated clinical environment while also exposing the patient to ionizing radiation (for the CT-scan and X-ray radiography). Furthermore, the use of at least three ultrasound images to localize the at least three anatomical landmarks allows to access in an accurate way the tridimensional spatial position of the at least three anatomical landmarks. This is crucial for correctly implementing the following steps, notably the one of registration of a digital model of the body part in the imaging sensor referential.

According to one embodiment, the at least one fiducial marker is rigidly fixed to the ultrasound device.

According to one embodiment, the calculation of the spatial orientation of the sagittal plane in the referential of the imaging sensor is performed by analyzing the portion of the body part comprised in the fourth image.

According to one embodiment, the step of outputting further comprises outputting the spatial orientation in the referential of the imaging sensor of an ensemble comprising the first, the second and third landmark. This information is intrinsically obtained from the position of the first, second and third landmark in the referential of the imaging sensor.

According to one embodiment, the body part is the shoulder of the patient.

According to one embodiment, the first landmark is the acromion angle, the second landmark is the trigonum spinae, and the third landmark is the inferior angle of the scapula.

According to one embodiment, the method further comprises receiving as input a predefined spatial transformation between the ultrasound device and the fiducial marker for calculating the position and spatial orientation of the ultrasound image in a referential of the imaging sensor.

According to one embodiment, the fiducial marker is a squared-based fiducial markers with an internal pattern.

According to one embodiment, the imaging sensor further comprises an accelerometer and the method further comprises:

receives as input at least one accelerometer measure;

using a vertical vector of the accelerometer measure for calculating the spatial orientation of a transversal plane in the referential of the imaging sensor.

According to one embodiment, the sagittal plane is obtained from the fourth image using a machine learning algorithm. Advantageously, this embodiment allows to implementing the method with images acquired with any standard camera, such as for example the camera of a smart phone.

According to one embodiment, the acquisition system comprises at least one second fiducial marker positioned on a portion of the thorax of the subject. The fourth image comprises the said at least one second fiducial marker. In this embodiment, the sagittal plane is obtained from the fourth image using said at least one second fiducial marker.

According to one embodiment, the imaging sensor is a range imaging sensor configured to acquire an image having a depth component and a visual component. In this embodiment at least the fourth image is acquired with said range imaging sensor and the sagittal plane in the referential of the imaging sensor is calculated using the depth component of the said fourth image comprising the portion of the body part. Advantageously, this embodiment allows to obtain directly the depth information reducing the computational time to implement the method and increasing the accuracy.

According to one embodiment, wherein the imaging sensor is a range imaging sensor configured to acquire an image having a depth component and the first image, the second image, the third image and the fourth image have been previously acquired with said range imaging sensor, and the method comprises:

calculating the sagittal plane in the referential of the imaging sensor using the depth component of the fourth image comprising the portion of the body part;

calculating the position and spatial orientation of the fiducial marker using the depth component of the first, the second, the third image so as to localize the ultrasound device and calculate the position and spatial orientation of the ultrasound image in a referential of the imaging sensor.

According to one embodiment, the method further comprises:

receiving a digital model of the bone morphology of the subject scapula obtained from tridimensional images of the subject wherein the first, second and third landmarks have been identified;

applying a spatial transformation so as to register the digital model of the scapula in the referential of the imaging sensor so that each point comprised in the digital model of the scapula has a known position in the imaging sensor referential.

This embodiment advantageously allows to transpose the detailed digital model of the bone morphology of the subject which has been determined from tridimensional images of the subject in lying position into a functional spatial orientation and position using the landmarks acquired from a functional position of the subject, for example while the subject is standing or sited.

According to one embodiment, the registered digital model and the spatial orientation of the transversal, sagittal and coronal plane in the referential of the imaging sensor are used to compute the range of motion of the body part in a studied functional position.

The present invention further relates to a computer program product comprising instructions which, when the program is executed by a computer, cause the computer to carry out the steps of the method according to any one of the embodiments described hereabove.

The present invention further relates to a computer-readable storage medium comprising instructions which, when executed by a computer, cause the computer to carry out the steps of the method according to any one of the embodiments described hereabove.

The present invention further relates to a system for providing anatomical landmarks of a subject's body part, said system comprising:

at least one input adapted to receive a set of measures previously acquired by an acquisition system comprising: an ultrasound device, at least one fiducial marker and an imaging sensor, said set of measures comprising:

at least one first ultrasound image comprising a first landmark and at least one first image acquired by the imaging sensor simultaneously to the first ultrasound image;

at least one second ultrasound image comprising a second landmark and at least one second image acquired simultaneously to the second ultrasound image;

at least one third ultrasound image comprising a third landmark and at least one third image acquired simultaneously to the third ultrasound image;

wherein the first, second and third image comprises the at least one fiducial marker;

at least one fourth image comprising at least one portion of the body part of the subject;

at least one processor configured to:

for each of said ultrasound image:

use the fiducial marker in the associated image for calculating the position and spatial orientation of the ultrasound image in a referential of the imaging sensor;

identify the position of the associated landmark and using the position and spatial orientation of the ultrasound image for calculating the position of the landmark in the referential of the imaging sensor;

calculate the spatial orientation of a transversal plane in the referential of the imaging sensor;

calculate the spatial orientation of a sagittal plane in the referential of the imaging sensor;

use the spatial orientation of the transversal and sagittal plane to calculate the spatial orientation of a coronal plane in the referential of the imaging sensor;

at least one output adapted to provide said anatomical landmarks of a subject's body part comprising at least the position of the first, second and third landmark, and the spatial orientation of the transversal, sagittal and coronal plane in the referential of the imaging sensor.

According to one embodiment, the at least one fiducial marker is rigidly fixed to the ultrasound device.

According to one embodiment, the processor is further configured to calculate the spatial orientation of the sagittal plane in the referential of the imaging sensor by analyzing the portion of the body part comprised in the fourth image.

The acquisition system may further comprise one or more additional fiducial markers that may be positioned on the subject or in its proximity. In this case, according to one embodiment, a second fiducial marker is fixed on the torso of the subject and the fourth image comprises it. The second fiducial marker comprised in the fourth image is then used to calculate the spatial orientation of the sagittal plane in the referential of the imaging sensor. Alternatively, said second fiducial marker may be placed in proximity of the subject.

According to one embodiment, the at least one output is further adapted to output the spatial orientation in the referential of the imaging sensor of an ensemble comprising the first, the second and third landmark. This information is intrinsically obtained from the position of the first, second and third landmark in the referential of the imaging sensor.

According to one embodiment wherein the body part is the shoulder of the patient and the first landmark is the acromion angle, the second landmark is the trigonum spinae and the third landmark is the inferior angle of the scapula, the at least one processor is further configured to:

- receive a digital model of the bone morphology of the subject scapula obtained from tridimensional images of the subject wherein the first, second and third landmarks have been identified;
- apply a spatial transformation so as to register the digital model of the scapula in the referential of the imaging sensor so that each point comprised in the digital model of the scapula has a known position in the imaging sensor referential.

According to one embodiment, the at least one processor is further configured to compute the range of motion of the body part in a studied position using the registered digital model and the spatial orientation of the transversal, sagittal and coronal plane in the referential of the imaging sensor.

Definitions

In the present invention, the following terms have the following meanings:

- "Digital model" refers to a three-dimensional digital (or virtual) model being a virtual object in 3 dimensions. The position and orientation of the model is known in the associated digital referential.
- "Processor" this term is herein not restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.
- "Referential" refers to a coordinate system that uses one or more numbers, or coordinates, to uniquely determine the position of the points or other geometric elements on a manifold such as Euclidean space.
- "Simultaneously" refers to two or more event occurring at the same time. In the case of the present invention, the ultrasound image is acquired at the same time that the image from the imaging sensor.
- "Subject" refers to a mammal, preferably a human. In the sense of the present invention, a subject may be an individual having any mental or physical disorder requiring regular or frequent medication or may be a patient, i.e. a person receiving medical attention, undergoing or having underwent a medical treatment, or monitored for the development of a disease.
- "Visual image": refers to a m-by-n-by d data array representing a picture made by a sensor (i.e. camera), where the m-by-n dimensions determine the dimension of the image and the d dimension depends on the color model used to represent the image. The dimension d may be of 1 for a grayscale color model or 3 for example for a RGB, CMY, RYB etc. color model.
- "Depth image": refers to a data array wherein each pixel (u, v) corresponds directly to the distance between the range imaging sensor and the object (i.e. subject).

BRIEF DESCRIPTION OF THE DRAWINGS

The following detailed description will be better understood when read in conjunction with the drawings. For the purpose of illustrating, the method and system of the present invention are shown in the preferred embodiments. It should be understood, however that the present invention is not limited to the precise arrangements, structures, features, embodiments, and aspect shown. The drawings are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Features and advantages of the invention will become apparent from the following description of embodiments of a system, this description being given merely by way of example and with reference to the appended drawings in which.

While various embodiments have been described and illustrated, the detailed description is not to be construed as being limited hereto. Various modifications can be made to the embodiments by those skilled in the art without departing from the true teaching and scope of the disclosure as defined by the claims.

DETAILED DESCRIPTION

The present invention relates to a computer-implemented method for providing the spatial orientation and position of anatomical landmarks of a subject's body part to be used in the planification of orthopedic surgeries.

Figure 1:
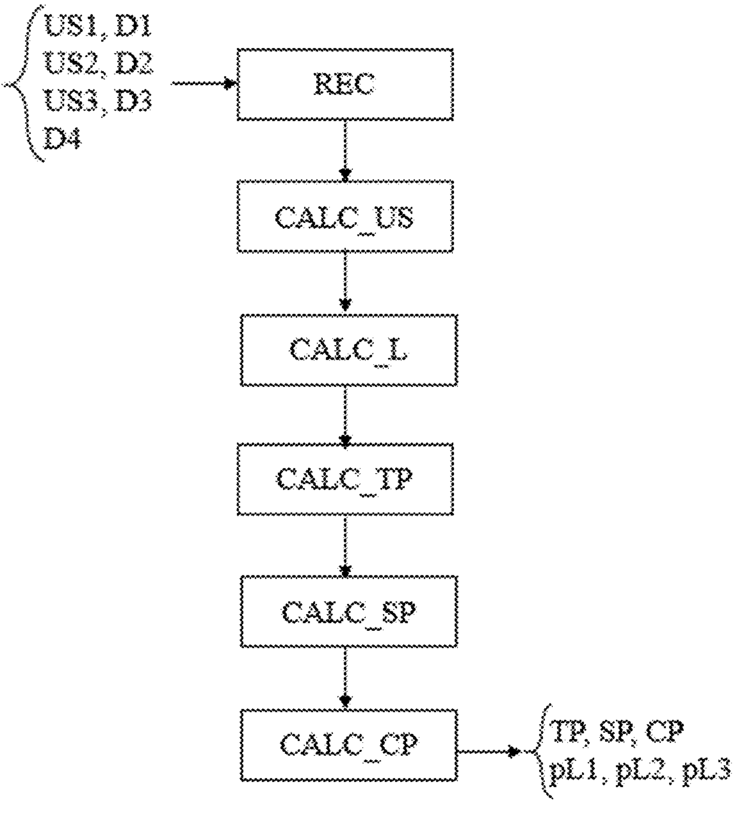
FIG. 1 is a block diagram of the method of the invention according to a first embodiment.

According to one embodiment represented in FIG. 1, the first step of the present invention comprises receiving REC a set of measures previously acquired by a system comprising an ultrasound device, at least one fiducial marker associated to the ultrasound device and an imaging sensor.

The ultrasound device is configured to generate ultrasound images of the subject and create an image of internal body structures such as tendons, muscles, joints, blood vessels, and internal organs.

The term fiducial markers refers to an artificial marker added to a scene acquired by a sensor in order to facilitate locating point correspondences between images, and/or between images and a known model.

Such fiducial markers may be for example spherical, circular, simply reflective surfaces, or square. As the circular systems can provide only a single point with a high degree of accuracy, multiple circular markers are needed for full pose estimation. Square fiducial markers, on the other hand, provide a key point for each of the four corners which are sufficient to perform the sensor pose estimation.

In one embodiment, the fiducial marker is rigidly fixed on the ultrasound device, notably in a movable way. Indeed, having an invariable spatial relationship between the ultrasound device and the fiducial marker (at least during the measurements) allows advantageously to maintain a constant transformation T between the ultrasound device and the fiducial marker which allows to calculate the position and spatial orientation of the ultrasound image USi in a referential of the imaging sensor, as will be explained in details hereafter. On the other hand, the imaging sensor is structurally independent from the ultrasound device and fiducial marker (i.e., no need to have a physical link between them).

According to one embodiment, the fiducial marker is a squared-based fiducial markers with an internal pattern, for instance the ArUco marker, which can be directly visible by the visual image of the imaging sensor.

A variety of imaging sensors or cameras are currently available. The imaging sensor may be placed in such a way to face towards the subject and comprise in its field a view of the body part of the subject and/or the fiducial marker. According to one embodiment, the imaging sensor may be configured to acquire a color image (i.e. black and white, RGB, etc.) or a depth map, wherein each point of the depth maps represents the distance between the imaging sensor and the object/subject in the field of view of the imaging sensor. Alternatively, the imaging sensor may be configured to acquire simultaneously both one color image (also called in the description visual component) and one depth map (also called herein depth component) of the same scene.

In one embodiment, the set of measures comprises:

- at least one first ultrasound image US1 comprising a first landmark L1 and at least one first image D1 comprising the fiducial marker acquired by the imaging sensor simultaneously to the first ultrasound image US1;
- at least one second ultrasound image US2 comprising a second landmark L2 and at least one second image D2 comprising the fiducial marker acquired by the imaging sensor simultaneously to the second ultrasound image US2;
- at least one third ultrasound image US3 comprising a third landmark L3 and at least one third image D3 comprising the fiducial marker acquired by the imaging sensor simultaneously to the third ultrasound image US3;
- at least one fourth image D4 comprising at least one portion of the body part of the subject.

According to one embodiment, the set of measures is acquired while the subject is placed in a specific position, such as standing or sitting positions.

The body part may be all bony structures or rigid organs which require a measurement of a functional 3D angles with respect to the three anatomical planes, such as for example the shoulder, the pelvis or the humerus.

The first D1, the second D2 and the third D3 image are acquired while the ultrasound device is put into contact with at least one body part of the subject in proximity with the respective landmark. To obtain images D1, D2 and D3, the imaging sensor is placed toward the patient so as to comprises in its field of view the fiducial marker (i.e., no need to comprise at least one portion of the body of the subject).

The at least one fourth image D4 is acquired so as to comprise at least one portion of the body part of the subject and comprise as well a portion of the torso or of the back of the subject. The fourth image D4 does not need to comprise the fiducial marker rigidly fixed on the ultrasound device. Therefore, the imaging sensor may be placed towards the subject so that at least one portion of the body of the subject, preferably the torso or a portion of it, is comprised in the field of view of the imaging sensor. In this case, the ultrasound device and the fiducial marker rigidly fixed to it are removed from the scene. In one example, the imaging sensor is position facing the subject, with no object interposing between the imaging sensor and the subject.

In the step CALC_SP, the fourth image D4 is used to calculate the spatial orientation of a sagittal plane SP in the referential of the imaging sensor.

In one embodiment, the fourth image D4, notably the portion comprising the subject body, is used to calculate the spatial orientation of a sagittal plane SP in the referential of the imaging sensor. In this embodiment wherein the fourth image D4 is a color image, the spatial orientation of sagittal plane is obtained from the fourth image D4 which is provided as input to a machine learning algorithm.

In one alternative embodiment, a second fiducial marker is positioned on the torso of the patient so that the fourth image D4 comprises said second fiducial marker. The second fiducial marker is preferably an ARUCO marker. The second fiducial marker comprised in the fourth image D4 is used to calculate the spatial orientation of a sagittal plane SP in the referential of the imaging sensor.

In one alternative embodiment, the second fiducial marker is positioned in the environment of the subject (i.e., in proximity of the subject and the imaging sensor) in a vertical position. For example, an ARUCO marker is fixed on a wall of the room where the measurements are performed. In this embodiment, the fourth image D4 comprises said second fiducial marker disposed in a predefined orientation according to the sagittal plan of the patient (but not necessary a portion of the body of the patient). The second fiducial marker may be disposed parallelly or perpendicularly to the sagittal plane of the patient. The second fiducial marker comprised in the fourth image D4 is used to calculate the spatial orientation of a sagittal plane SP in the referential of the imaging sensor.

In one embodiment, the imaging sensor is a range imaging sensor configured to acquire an image having a depth component and a visual component.

A variety of range imaging sensors or cameras are currently available which are based on different types of range imaging technics such as stereo triangulation, sheet of light triangulation, structured light, interferometry, coded aperture and any other technics known by the man skilled in the art.

In one preferred embodiment, the range imaging sensor is a time-of-flight camera (ToF). The range imaging sensor is configured to acquire a depth map, or depth image that may be presented under the form of a bidimensional array representing a grey level image or an RGB image, wherein the size of the array depends on the ToF camera, notably the photosensor used for image acquisition. The raw image may be for example coded in 16 bits where the information on the depth measure in each pixel (u, v) correspond directly to the distance between the ToF camera and the object (i.e. the patient).

The ToF camera may be a pulsed-light camera using pulsed-light sensor or a continuous-wave modulated-light camera using continuous-wave modulation sensor. The ToF cameras may combine a single or multiple laser beams, possibly mounted onto a rotating mechanism, with a 2D array of light detectors and time-to-digital converters, to produce 1-D or 2-D arrays of depth values. The ToF camera may implement laser diodes or a LED of different wavelengths, notably infrared or near infrared.

According to one embodiment, the time-of-flight camera uses infrared light illumination Several ToF cameras are actually available such as CamCube PMD from Photonic Mixer Devices (PMD) Technologies, SwissRanger 4000 or the sensor Kinect V1 of Microsoft. According to one embodiment, the ToF camera is a Kinect Azur RGB-D camera which uses multiple modulation frequencies (10-130 MHz) thus achieving an excellent compromise between depth accuracy and phase unwrapping.

During the acquisition of images D1, D2 and D3, the range imaging sensor is placed in such a way to face the subject and comprise in its field a view of the body part of the subject and the fiducial marker rigidly fixed to the ultrasound device.

According to the embodiment wherein the imaging sensor is a range imaging sensor, the at least fourth image D4 is acquired with said range imaging sensor and the spatial orientation of sagittal plane SP in the referential of the imaging sensor is calculated using the depth component of said fourth image D4 comprising the portion of the body part.

In one embodiment, where the body part is the shoulder of the patient, D4 may be acquired so as to comprise both the left and right shoulder. Both left and right shoulders of the subject may be inferred from depth images and used to define the mediolateral axis of the subject thanks to a deep learning-based approach, (for example the one implemented in the Kinect Azure Body Tracking library).

In one embodiment, the fourth image D4 is used to calculate the spatial orientation of a transversal plane TP in the referential of the range imaging sensor using a similar deep learning-based approach, (for example the one implemented in the Kinect Azure Body Tracking library).

In one embodiment, the imaging sensor is a range imaging sensor configured to acquire an image having only a depth component and the first image D1, the second image D2, the third image D3 and the fourth image D4 have been previously acquired with said range imaging sensor. In this case, the spatial orientation of sagittal plane SP in the referential of the imaging sensor may be calculated using the depth component of the fourth image D4 comprising the portion of the body part. In this embodiment, the fiducial marker is a tridimensional marker and the position and spatial orientation of the fiducial marker is calculated using the depth component of the first D1, the second D2, the third image D3.

The imaging sensor may further comprise an accelerometer configured to acquire at least one accelerometer measure that is received by the at least one processor implementing the method. The vertical vector measured by the accelerometer may be then used for calculating the spatial orientation of the transversal plane TP in the referential of the imaging sensor.

The cross-product of the transversal and sagittal plane SP normal vectors may be computed to extract the coronal plane CP. Finally, the cross-product of the normal vectors transversal of the plane TP and coronal plane CP defines a new sagittal one and all vectors are normalized to obtain an orthonormal coordinates system.

In one embodiment, the position and spatial orientation of the ultrasound image (US1, US2, US3) in the referential of the imaging sensor is calculated. In order to perform this step CALC_US, the fiducial marker visible in the images may be used (D1, D2, D3).

According to one embodiment, the method further comprising receiving as input a predefined spatial transformation T between the ultrasound device and the fiducial marker for calculating the position and spatial orientation of the ultrasound image (US1, US2, US3) in the referential of the imaging sensor of step CALC_US.

According to one embodiment, the method comprises the step CALC_L that, for each ultrasound image, identifies the position of the associated landmark (L1, L2, L3) in the ultrasound images (US1, US2, US3). The position of the associated landmark (L1, L2, L3) may be manually identified by a user or automatically identified by an image analysis algorithm. This embodiment further comprises using the position and spatial orientation of the ultrasound image (US1, US2, US3) for calculating the position of the landmark (pLi) in the referential of the imaging sensor. The (anatomical) landmarks may be associated to specific points in the anatomy of human body or alternatively to a surface or a volume of one or more anatomical structures in the human body. In the case wherein one landmark is associated to a surface or a volume, the position and spatial orientation of the associated landmark (L1, L2, L3) may be identified by the user by manual delineation or identified by automatic segmentation using an image analysis algorithm. Then, the position and spatial orientation of the ultrasound image (US1, US2, US3) may be used to calculate the position and spatial orientation of the landmark (pLi) in the referential of the imaging sensor. Registration methods may be notably used to implement this operation.

Advantageously, the calculation steps CALC_US, CALC_L, CALC_TP, CALC_SP and CALC_CP allow to obtain the information concerning the three anatomical planes (TP, CP, SP) and the landmarks (L1, L2, L3) in a same referential.

Figure 3:
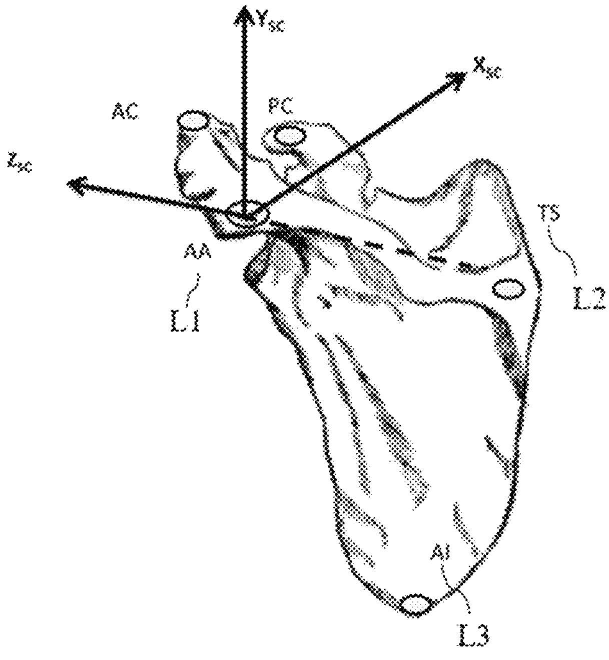
FIG. 3 is a schematic presentation of joint coordinate system (JCS) based on anatomic landmarks defined by the ISB. AA, acromion angle; AI, inferior angle of the scapula; TS, trigonum spinae (root of the scapular spine).

According to one embodiment wherein the body part is the shoulder, the first landmark L1 is the acromion angle, the second landmark L2 is the trigonum spinae, and the third landmark L3 is the inferior angle of the scapula. These anatomical landmarks are shown in FIG. 3.

According to one embodiment, the method comprises a step of outputting the anatomical landmarks of a subject's body part comprising at least the position of the first pL1, second pL2 and third landmark pL3, and the spatial orientation of the transversal TP, sagittal SP and coronal plane CP in the referential of the imaging sensor. As the position of the first pL1, second pL2 and third landmark pL3 is known, then the spatial orientation of the ensemble formed by the landmarks (pL1, pL2, pL3) is known a well in the referential of the imaging sensor. Therefore, the information concerning the spatial orientation of the ensemble formed by the landmarks (pL1, pL2, pL3) in the referential of the imaging sensor may be outputted as well.

Figure 2:
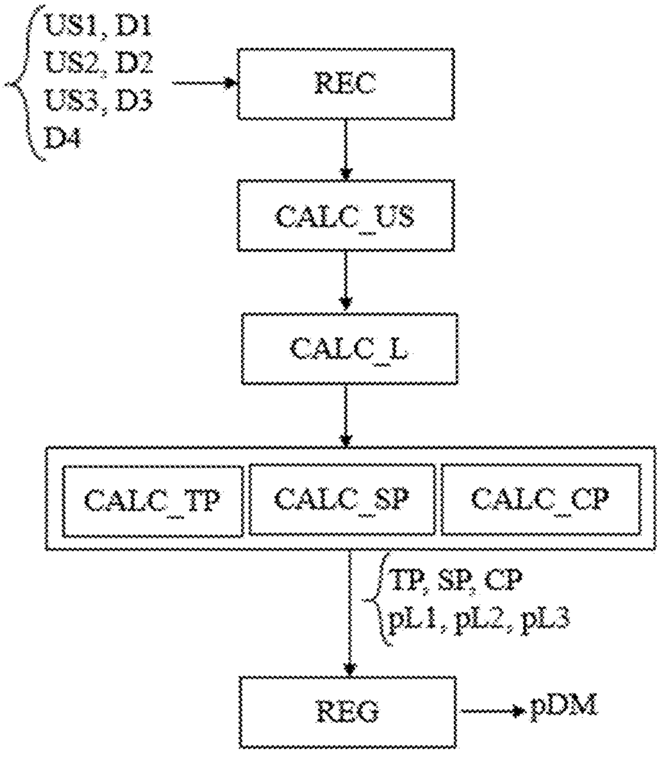
FIG. 2 is a block diagram of the method of the invention according to a second embodiment.

According to one embodiment shown in FIG. 2, the method also comprises receiving a digital model of the bone morphology of the subject scapula obtained from tridimensional images of the subject wherein the first L1, second L2 and third landmarks L3 have been identified. This REG step also comprises applying a spatial transformation so as to register the digital model of the scapula in the referential of the imaging sensor so that each point comprised in the digital model pDM of the scapula has a known position in the imaging sensor referential. The spatial transformation may be a rigid transformation.

In a preferred embodiment, the registered digital model and the spatial orientation of the transversal TP, sagittal SP and coronal plane CP in the referential of the imaging sensor are used to compute the range of motion of the body part in a studied position.

Indeed, the registration of the three landmarks to the digital model and the known orientation of the three anatomical planes are advantageously used in a treatment planning system algorithm from which the user (i.e. the surgeon) may obtain the amplitude of movement of the body part under analysis being defined with respect to these three anatomical planes (TP, CP, SP), such as the maximal flexion, the extension, the abduction, adduction, the internal and external rotation that may be realized by one bone of the body part in one studied functional position and in the case of the positioning of a prosthesis. In the case of the shoulder, the treatment planning system would allow to know the maximal flexion, the extension, the abduction, adduction, the internal and external rotation that may be realized by the humerus in one studied functional position and after the positioning of the prosthesis.

With respect to other technics that try to estimate the positions of anatomical landmarks using X-ray images of the subject body part, the present invention advantageously does not expose the subject to unnecessary radiations.

The present invention further comprises a computer program product comprising instructions which, when the program is executed by a computer, cause the computer to carry out the steps of the method according to any one of the embodiments described above.

The present invention further comprises a computer-readable storage medium comprising instructions which, when executed by a computer, cause the computer to carry out the steps of the method according to any one of the embodiments described here above. According to one embodiment, the computer-readable storage medium is a non-transitory computer-readable storage medium.

Computer programs implementing the method of the present invention can commonly be distributed to users on a distribution computer-readable storage medium such as, but not limited to, an SD card, an external storage device, a microchip, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the method as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

The present invention also relates to a system comprising means for carrying out the steps of the method as described above.

More in details the present invention relates to a system for providing anatomical landmarks of a subject's body part.

In one embodiment, said system comprises:

- at least one input adapted to receive a set of measures previously acquired by an ultrasound device comprising at least one fiducial marker and an imaging sensor, said set of measures comprising:
  - at least one first ultrasound image US1 comprising a first landmark L1 and at least one first image D1 acquired by the imaging sensor simultaneously to the first ultrasound image US1;
  - at least one second ultrasound image US2 comprising a second landmark L2 and at least one second image D2 acquired simultaneously to the second ultrasound image US2;
  - at least one third ultrasound image US3 comprising a third landmark L3 and at least one third image D3 acquired simultaneously to the third ultrasound image US3.
  - wherein the first D1, second D2 and third D3 image comprises the at least one fiducial marker.
  - at least one fourth image D4 comprising at least one portion of the body part of the subject.

The set of measures may be stored in a computer readable storage medium on a database, notably a medical database. Alternatively, the data of the set of measure may be received in real time during the image acquisition from the ultrasound device and the imaging sensor. In this case the system comprises a communication device allowing to transfer the measures from the acquisition devices to the system through wire connection or wirelessly.

According to one embodiment, the fiducial marker is a squared-based fiducial markers with an internal pattern also known as ArUco.

According to one embodiment, the system comprises at least one processor configured to carry out all the step of the method described hereabove.

More in detail the at least one processor is configured to perform the following steps, for each of said ultrasound image US1:

- using the fiducial marker in the associated image Di (i.e., D1, D2, D3) for calculating the position and spatial orientation of the ultrasound image USi (i.e. US1, US2, US3) in a referential of the imaging sensor;
- identifying the position of the associated landmark Li and using the position and spatial orientation of the ultrasound image for calculating the position of the landmark pLi (i.e. pL1, pL2, pL3) in the referential of the imaging sensor;

According to one embodiment, the at least one processor is further configured to perform the following steps:

calculating the spatial orientation of a transversal plane TP in the referential of the imaging sensor;

calculating the spatial orientation of a sagittal plane SP in the referential of the imaging sensor by analyzing for the portion of the body part comprised in the fourth image D4;

using the spatial orientation of the transversal and sagittal plane to calculate the spatial orientation of a coronal plane CP in the referential of the imaging sensor;

In one embodiment, the processor is further configured to receive as input a predefined spatial transformation T between the ultrasound device and the fiducial marker for calculating the position and spatial orientation of the ultrasound image USi in a referential of the imaging sensor.

Furthermore, when the imaging sensor further comprising an accelerometer, the at least one processor may be configured to:

receive as input at least one accelerometer measure;

use a vertical vector of the accelerometer measure for calculating the spatial orientation of a transversal plane TP in the referential of the imaging sensor.

The accelerometer measures may be stored in a computer readable storage medium on a database, notably a medical database. Alternatively, the accelerometer measures may be received in real time during the image acquisition from the accelerometer. In this case the system comprises a communication device allowing to transfer the measures from the accelerometer to the system through wire connection or wirelessly.

According to one embodiment, the body part is one shoulder of the patient and the first L1, second L2 and third L3 landmark are respectively the acromion angle, the trigonum spinae and the inferior angle of the scapula, the processor is further configured to:

receive a digital model of the bone morphology of the subject scapula obtained from tridimensional images of the subject wherein the first L1, second L2 and third landmarks L3 have been identified;

apply a spatial transformation so as to register the digital model of the scapula in the referential of the imaging sensor so that each point comprised in the digital model pDM of the scapula has a known position in the imaging sensor referential.

According to one embodiment, the system comprises at least one output adapted to provide said anatomical landmarks of a subject's body part comprising at least the position and spatial orientation of the first L1, second L2 and third L3 landmark, and the spatial orientation of the transversal TP, sagittal SP and coronal plane CP in the referential of the imaging sensor. This output may simply be an information transfer to another digital to analogue module. Said digital to analogue module may be a display to visualize the landmarks in the ultrasound images.

The invention claimed is:

1. A method comprising:

receiving a set of measures previously acquired by an acquisition system comprising: an ultrasound device, at least one fiducial marker, rigidly fixed on said ultrasound device, and an imaging sensor; said set of measures comprising:

at least one first ultrasound image comprising a first landmark and at least one first image acquired by said imaging sensor simultaneously to said at least one first ultrasound image;

at least one second ultrasound image comprising a second landmark and at least one second image acquired simultaneously to said at least one second ultrasound image; and at least one third ultrasound image comprising a third landmark and at least one third image acquired simultaneously to said at least one third ultrasound image;

wherein the at least one first image, the at least one second image, and the at least one third image comprise the at least one fiducial marker;

at least one fourth image comprising at least one portion of a body part of a subject;

for each ultrasound image:

using the at least one fiducial marker in the associated image for calculating the position and spatial orientation of each ultrasound image in a referential of the imaging sensor; and identifying the position of the associated landmark in each ultrasound image and using the position and spatial orientation of each ultrasound image for calculating the position of the associated landmark in the referential of the imaging sensor;

calculating the spatial orientation of a transversal plane in the referential of the imaging sensor;

calculating the spatial orientation of a sagittal plane in the referential of the imaging sensor by analyzing the portion of the body part comprised in the at least one fourth image, wherein the spatial orientation of the sagittal plane is obtained from the at least one fourth image using machine learning;

using the position and spatial orientation of the transversal plane and the sagittal plane to calculate the position and spatial orientation of a coronal plane in the referential of the imaging sensor, wherein the spatial orientation of the transversal plane, the spatial orientation of the sagittal plane, and the spatial orientation of the coronal plane are used to compute a range of motion of the body part of the subject; and displaying, in a computer system, a visual version of the anatomical landmarks of the body part of the subject comprising at least the position of the first landmark, the second landmark, and the third landmark, and the spatial orientation of an ensemble comprising the first landmark, the second landmark, and the third landmark in the referential of the imaging sensor, and the spatial orientation of the transversal plane, the spatial orientation of the sagittal plane, and the spatial orientation of the coronal plane in the referential of the imaging sensor, wherein the visual version of the anatomical landmarks of the body part of the subject comprising at least the position of the first landmark, the second landmark, and the third landmark, and the spatial orientation of the ensemble comprising the first landmark, the second landmark, and the third landmark in the referential of the imaging sensor, and the spatial orientation of the transversal plane, the spatial orientation of the sagittal plane, and the spatial orientation of the coronal plane in the referential of the imaging sensor is used for planning an orthopedic surgery.

2. The method according to claim 1, wherein the body part is the shoulder of the subject.

3. The method according to claim 2, wherein the first landmark is the acromion angle, the second landmark is the trigonum spinae, and the third landmark is the inferior angle of the scapula.

4. The method according to claim 2, further comprising: receiving a digital model of the bone morphology of a scapula of the subject obtained from tridimensional images of the subject wherein the first landmark, the second landmark, and the third landmark have been identified; and applying a spatial transformation so as to register the digital model of the scapula in the referential of the imaging sensor so that each point comprised in the digital model of the scapula has a known position in the referential of the imaging sensor.

5. The method according to claim 1, further receiving as input a predefined spatial transformation between the ultrasound device and the at least one fiducial marker for calculating the position and spatial orientation of each ultrasound image in the referential of the imaging sensor.

6. The method according to claim 1, wherein the imaging sensor further comprises an accelerometer and the method further comprises:

receiving as input at least one accelerometer measure; and using a vertical vector of the at least one accelerometer measure for calculating the spatial orientation of the transversal plane in the referential of the imaging sensor.

7. The method according to claim 1, wherein the at least one fiducial marker is a squared-based fiducial marker with an internal pattern.

8. The method according to claim 1, wherein the imaging sensor is a range imaging sensor configured to acquire an image having a depth component and a visual component, the at least one fourth image is acquired with said range imaging sensor and the spatial orientation of the sagittal plane in the referential of the imaging sensor is calculated using the depth component of the at least one fourth image comprising the portion of the body part.

9. The method according to claim 1, wherein the imaging sensor is a range imaging sensor configured to acquire an image having a depth component and the at least one first image, the at least one second image, the at least one third image and the at least one fourth image have been previously acquired with said range imaging sensor, and the method comprises:

calculating the spatial orientation of the sagittal plane in the referential of the imaging sensor using the depth component of the at least one fourth image comprising the portion of the body part; and calculating the position and spatial orientation of the at least one fiducial marker using the depth component of the at least one first image, the at least one second image, and the at least one third image so as to localize the ultrasound device and calculate the position and spatial orientation of each ultrasound image in the referential of the imaging sensor.

10. A system comprising:

at least one input adapted to receive a set of measures previously acquired by an acquisition system comprising: an ultrasound device, at least one fiducial marker, rigidly fixed on said ultrasound device, and an imaging sensor; said set of measures comprising:

at least one first ultrasound image comprising a first landmark and at least one first image acquired by said imaging sensor simultaneously to the at least one first ultrasound image;

at least one second ultrasound image comprising a second landmark and at least one second image acquired simultaneously to the at least one second ultrasound image; and at least one third ultrasound image comprising a third landmark and at least one third image acquired simultaneously to the at least one third ultrasound image;

wherein the at least one first image, the at least one second image, and the at least one third image comprise the at least one fiducial marker;

at least one fourth image comprising at least one portion of a body part of a subject;

at least one processor configured to:

for each of said ultrasound image:

use the at least one fiducial marker in the associated image for calculating the position and spatial orientation of each ultrasound image in a referential of the imaging sensor; and identify the position of the associated landmark and use the position and spatial orientation of each ultrasound image for calculating the position of the associated landmark in the referential of the imaging sensor;

calculate the spatial orientation of a transversal plane in the referential of the imaging sensor;

calculate the spatial orientation of a sagittal plane in the referential of the imaging sensor by analyzing for the portion of the body part comprised in the at least one fourth image, wherein the spatial orientation of the sagittal plane is obtained from the at least one fourth image using machine learning;

use the spatial orientation of the transversal plane and the sagittal plane to calculate the spatial orientation of a coronal plane in the referential of the imaging sensor, wherein the spatial orientation of the transversal plane, the spatial orientation of the sagittal plane, and the spatial orientation of the coronal plane are used to compute a range of motion of the body part of the subject; and display, in a computer system, a visual version of the anatomical landmarks of the body part of the subject comprising at least the position of the first landmark, the second landmark, and the third landmark, the spatial orientation of an ensemble comprising the first landmark, the second landmark, and the third landmark, and the spatial orientation of the transversal plane, the spatial orientation of the sagittal plane, and the spatial orientation of the coronal plane in the referential of the imaging sensor, wherein the visual version of the anatomical landmarks of the body part of the subject comprising at least the position of the first landmark, the second landmark, and the third landmark, and the spatial orientation of the ensemble comprising the first landmark, the second landmark, and the third landmark in the referential of the imaging sensor, and the spatial orientation of the transversal plane, the spatial orientation of the sagittal plane, and the spatial orientation of the coronal plane in the referential of the imaging sensor is used for planning an orthopedic surgery.

11. The system according to claim 10, wherein the body part is the shoulder of the subject, the first landmark is the acromion angle, the second landmark is the trigonum spinae, the third landmark is the inferior angle of the scapula, and the at least one processor is further configured to:

receive a digital model of the bone morphology of a scapula of the subject obtained from tridimensional images of the subject wherein the first landmark, the second landmark, and the third landmark have been identified; and apply a spatial transformation so as to register the digital model of the scapula in the referential of the imaging sensor so that each point comprised in the digital model of the scapula has a known position in the referential of the imaging sensor.

12. The system according to claim 11, further receiving as input a predefined spatial transformation between the ultrasound device and the at least one fiducial marker for calculating the position and spatial orientation of each ultrasound image in the referential of the imaging sensor.

13. The system according to claim 11, wherein the imaging sensor further comprises an accelerometer and the at least one processor is further configured to:

receive as input at least one accelerometer measure; and use a vertical vector of the at least one accelerometer measure for calculating the spatial orientation of the transversal plane in the referential of the imaging sensor.

14. The system according to claim 11, wherein the at least one fiducial marker is a squared-based fiducial marker with an internal pattern.

15. A non-transitory computer readable medium comprising instructions which, when executed by a computer, cause the computer to carry out a method comprising:

receiving a set of measures previously acquired by an acquisition system comprising: an ultrasound device, at least one fiducial marker, rigidly fixed on the ultrasound device, and an imaging sensor, the set of measures comprising:

at least one first ultrasound image comprising a first landmark and at least one first image acquired by the imaging sensor simultaneously to the at least one first ultrasound image;

at least one second ultrasound image comprising a second landmark and at least one second image acquired simultaneously to the at least one second ultrasound image; and at least one third ultrasound image comprising a third landmark and at least one third image acquired simultaneously to the at least one third ultrasound image;

wherein the at least one first image, the at least one second image and the at least one third image comprise the at least one fiducial marker;

at least one fourth image comprising at least one portion of a body part of a subject;

for each ultrasound image:

using the at least one fiducial marker in the associated image for calculating the position and spatial orientation of each ultrasound image in a referential of the imaging sensor; and identifying the position of the associated landmark in each ultrasound image and using the position and spatial orientation of each ultrasound image for calculating the position of the landmark in the referential of the imaging sensor;

calculating the spatial orientation of a transversal plane in the referential of the imaging sensor;

calculating the spatial orientation of a sagittal plane in the referential of the imaging sensor by analyzing the portion of the body part comprised in the at least one fourth image, wherein the spatial orientation of the sagittal plane is obtained from the at least one fourth image using machine learning;

using the position and spatial orientation of the transversal plane and the sagittal plane to calculate the position and spatial orientation of a coronal plane in the referential of the imaging sensor, wherein the spatial orientation of the transversal plane, the spatial orientation of the sagittal plane, and the spatial orientation of the coronal plane are used to compute a range of motion of the body part of the subject; and displaying, in a computer system, a visual version of the anatomical landmarks of the body part of the subject comprising at least the position of the first landmark, the second landmark, and the third landmark, and the spatial orientation of an ensemble comprising the first landmark, the second landmark, and the third landmark in the referential of the imaging sensor, and the spatial orientation of the transversal plane, the spatial orientation of the sagittal plane, and the spatial orientation of the coronal plane in the referential of the imaging sensor, wherein the visual version of the anatomical landmarks of the body part of the subject comprising at least the position of the first landmark, the second landmark, and the third landmark, and the spatial orientation of the ensemble comprising the first landmark, the second landmark, and the third landmark in the referential of the imaging sensor, and the spatial orientation of the transversal plane, the spatial orientation of the sagittal plane, and the spatial orientation of the coronal plane in the referential of the imaging sensor is used for planning an orthopedic surgery.

* * * * *